United States Patent [19]

Luschen

[11] 4,271,113
[45] Jun. 2, 1981

[54] PROCESS FOR FORMING A PASSAGEWAY IN AN OSMOTIC DEVICE

[75] Inventor: Joseph G. Luschen, Los Gatos, Calif.

[73] Assignee: ALZA Corporation, Palo Alto, Calif.

[21] Appl. No.: 61,767

[22] Filed: Jul. 30, 1979

Related U.S. Application Data

[63] Continuation-in-part of Ser. No. 896,801, Apr. 17, 1978, abandoned.

[51] Int. Cl.³ .............................................. D04H 1/20
[52] U.S. Cl. .................................... 264/112; 264/119; 264/128; 264/DIG. 51
[58] Field of Search ............... 264/112, 119, DIG. 51, 264/128

[56] References Cited

U.S. PATENT DOCUMENTS

| | | | |
|---|---|---|---|
| 2,059,983 | 11/1936 | Dent et al. | 264/DIG. 51 |
| 2,844,489 | 7/1958 | Gemmer | 264/DIG. 51 |
| 3,146,169 | 8/1964 | Stephenson et al. | 424/22 |
| 3,916,899 | 11/1975 | Theeuwes | 424/15 |

*Primary Examiner*—Donald E. Czaja
*Assistant Examiner*—James R. Hall
*Attorney, Agent, or Firm*—Paul L. Sabatine; Edward L. Mandell; Thomas E. Ciotti

[57] ABSTRACT

A process is disclosed for forming an outlet passageway in an osmotic dispensing device. The process comprises compressing a drug formulation into a solid mass, forming a recess in the solid mass, and then spray coating the mass with a wall forming material that surrounds the mass. The outlet passageway in the wall is formed at the recess simultaneously and automatically during the coating procedure. The passageway extends through the wall and communicates with the drug and the exterior of the device for dispensing the drug over a prolonged period of time.

15 Claims, 9 Drawing Figures

PROCESS FOR FORMING A PASSAGEWAY IN AN OSMOTIC DEVICE

CROSS-REFERENCE TO RELATED APPLICATION

This application is a continuation-in-part of United States Patent Application Ser. No. 896,801 filed on Apr. 17, 1978 and now abandoned. This application and application Ser. No. 896,801 are both assigned to the Alza Corporation of Palo Alto, California. Application Ser. No. 896,801 is incorporated herein by reference, and benefit is claimed of its filing date.

BACKGROUND OF THE INVENTION

Generally, the prior art uses two separate and non-releated forms for delivering drugs, mainly the tablet and the osmotic device. The tablet is a solid dosage form, which may be molded or compressed, and contains a drug that is delivered by the tablet dissolving or disintegrating in a short time. A tablet made with a hole for releasing drug also is known to the prior art. For this tablet, the hole is made in a step that is the end step for manufacturing the tablet. For example, in U.S. Pat. No. 3,146,169 issued to Stephenson et al there is disclosed a tablet made by compressing an inert material around a medicated material with a hole punched through the outer, inert material. The hole extends into the medicated portion, and after the tablet is swallowed the medicament is released into the gastrointestinal tract by gastric fluid leaching it through the hole. The nature and rate of drug release for this tablet is determined by fluid leaching in an out of the hole as governed by the environment.

Osmotic devices for dispensing drugs are totally unlike the above described tablets. Osmotic devices are so named by the art because they dispense drug by physical and chemical principles comprehensive and fundamental to an osmotic device. Also, they are labelled as devices because the osmotic device governs the release pattern of the drug independent of the environment, and because they maintain their integrity during the dispensing period. In U.S. Pat. Nos. 3,845,770 and 3,916,899 issued to Theeuwes et al, there is disclosed an osmotic device comprising a semipermeable wall surrounding a compartment containing drug with an outlet passageway through the wall. The passageway, or hole, in osmotic devices, (a hole through the wall is by convention referred to as a passageway), is mechanically or laser drilled through the wall as the final manufacturing step, after the wall is formed on the device. Drug is released by fluid being imbibed through the wall, as the result of an osmotic pressure gradient across the wall, forming a solution containing drug in the compartment, which solution is osmotically pumped through the outlet passageway from the device over time.

While the above-described osmotic device represents a true advancement in the drug delivery art, it will be appreciated that if a process is made available for manufacturing an outlet passageway as an inherent part of the manufacture of the device, such a process would be a useful contribution to the art. Likewise, it will be appreciated by those versed in the art, that if a process is provided that eliminates a manufacturing step, or combines manufacturing steps into lesser or a single step, such a process also would be a valuable and practical contribution to the art.

OBJECTS OF THE INVENTION

Accordingly, it is an immediate object of this invention to provide a process for making an osmotic drug dispensing device by a novel process that is an improvement and contribution to the art.

Yet another object of the invention is to provide a process for forming an outlet device, which process is an integral part of the manufacture and occurs concomittantly in the manufacture of the device.

Still another object of the invention is to form an outlet passageway in the wall of an osmotic device which passageway is formed during the coating of the wall as a result of a recess made in a solid drug mass prior to coating the wall on the mass.

Yet another object of the invention is to provide a process for forming an outlet passageway in the wall of an osmotic dispensing device, which process is easy to use, economical and suitable for mass-producing an osmotic dispensing device.

Still another object of the invention is to provide an unique process for forming an outlet passageway in the wall of an osmotic dispensing device, which passageway is formed at a recess in a drug mass while surrounding the mass with a wall forming material and free of the need for positioning the mass in a wall forming machine.

Other objects, features and advantages of the invention will be more apparent to those skilled in the art from the detailed specification taken in conjunction with the drawings and the accompanying claims.

SUMMARY OF THE INVENTION

This invention concerns a process for making an osmotic drug dispensing device. The process comprises compressing a drug formulation into a solid mass, forming a recess or indentation in the mass, and then spray coating the mass with a wall forming material to surround the mass and form an outlet passageway in the wall. The passageway is formed automatically during the coating as the result of the recess in the mass, which recess is of sufficient width and depth to remain at least partly uncovered and at least partly uncoated by the wall for dispensing drug to a biological environment of use.

BRIEF DESCRIPTION OF THE DRAWINGS

In the drawings, which are not drawn to scale, but are set forth to illustrate various embodiments of the invention, the figures are as follows.

In the drawings and specification, like parts in related figures are identified by like numbers. The terms appearing earlier in the specification and in the discription of the drawings, as well as embodiments thereof, are further described elsewhere in the disclosure.

DETAILED DESCRIPTION OF THE INVENTION

Figure 1:
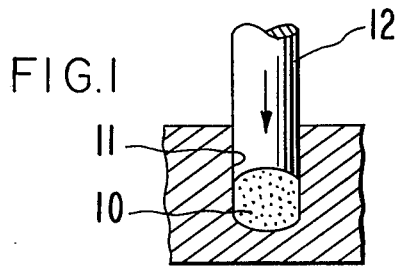
FIG. 1 is a partly sectional view of a mold depicting a plunger compressing a drug formulation into a solid mass.
Figure 2:
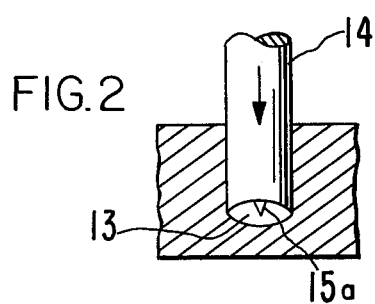
FIG. 2 is a partly sectional view of an indentation being formed in the compressed drug mass made in FIG. 1.
Figure 3:
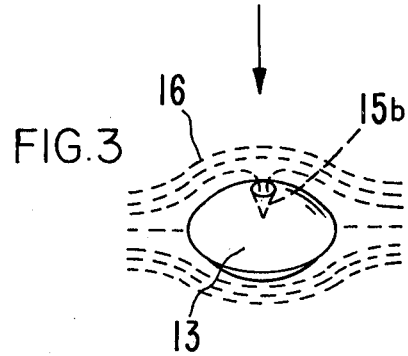
FIG. 3 is an enlarged, partly schematic elevational view of the solid mass formed in FIG. 2 being coated in a coating stream.
Figure 4:
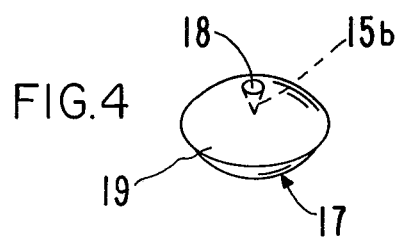
FIG. 4 is an enlarged, elevational view of the coated osmotic dispenser of FIGS. 1 through 3.

FIGS. 1 through 3 depict a process of the invention carried out in three steps for making a tablet-shaped osmotic device useful for administering orally a drug. In the first step as seen in FIG. 1, a drug formulation 10 is charged into the cavity of mold 11 and is compressed by plunger 12 into a solid mass 13 as seen in FIG. 2. After mass 13 is formed, plunger 12 is removed from the mold cavity. In the second step as seen in FIG. 2, a second plunger 14 equipped with a conical die 15a is inserted into the cavity of mold 11 and pressed against the top of mass 13 to form a conical indentation 15b, seen in FIG. 3 in mass 13. After indentation 15b is formed, plunger 14 is withdrawn and mass 13 removed from the cavity of mold 11. The third step of the process is illustrated in FIG. 3. The step of FIG. 3 comprises a coating indented mass 13 with a wall forming material. The coating procedure used is an air suspension coating technique in which the wall forming material is entrained in an air stream 16 and mass 13 is placed in the path of the air stream. The entrained material-air stream 16 is depicted by curved, dashed lines in FIG. 3. The entrained material uniformly coats onto the surface of mass 13, except at the site of indentation 15b and it forms a thin wall 19, as seen in FIG. 4 around mass 13. The dimensions of indentation 15b are such that the entrained material only partially penetrates into indentation 15b. Thus, the coating of the material that is applied does not reach the bottom of indentation 15b, seen in dashed lines in FIG. 4, nor does the mouth of the indentation become coated over. As a result of the coating step of the process, a passageway is automatically formed in wall 19 at the site of the indentation 15b. The finished osmotic device designated 17 in FIG. 4 comprises the compressed mass of drug, not visible in FIG. 4, surrounded by wall 19 with a passageway 18 extending through the wall to the mass at the site of indentation 15b.

Figure 5:
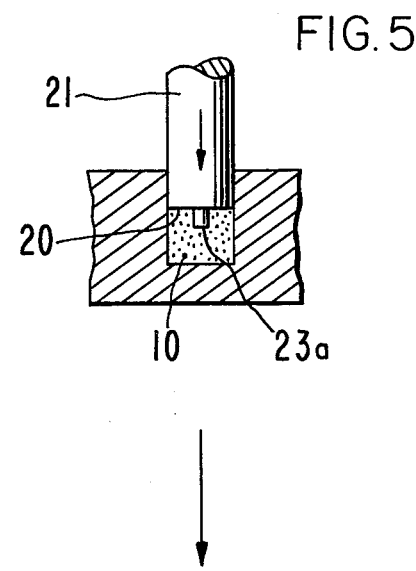
FIG. 5 illustrates a partly sectional view of a drug being compressed into a solid mass with another mold and plunger.
Figure 6:
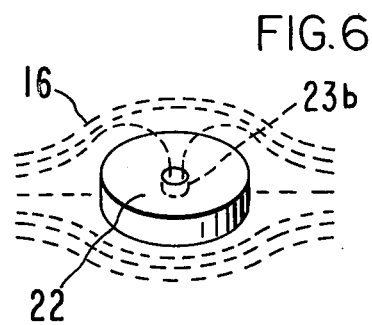
FIG. 6 is an enlarged partly schematic view of the solid mass formed in FIG. 5 being coated with a wall forming material.
Figure 7:
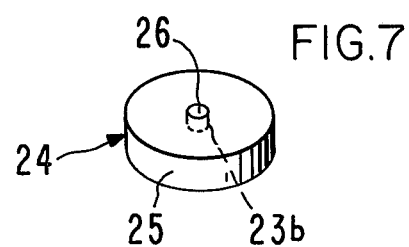
FIG. 7 is an enlarged elevational view of the finished osmotic device made as shown in FIGS. 5 and 6.

FIGS. 5 and 6 show an alternate process for carrying out the manufacture of an osmotic device. The process as carried out in FIGS. 5 and 6 comprise only two steps. In the first step, illustrated in FIG. 5, the osmotically effective drug formulation 10 is charged into the cavity of mold 20 and compressed by plunger 21 that is rammed into the mold cavity. The shape of the end of plunger 21 is such that it compresses formulation 10 into discoid-shaped solid mass 22, as seen in FIG. 6, and the cylindrical die 23a integral on plunger 21, simultaneously forms a cylindrical indentation 23b in mass 22. In the second step, as seen in FIG. 6, mass 22 is coated with a semipermeable polymeric wall forming material 16 by the same technique shown in FIG. 3 and discussed above. The finished osmotic device resulting from the process of FIGS. 5 and 6 is seen in FIG. 7 designated by numeral 24. Device 24 consists essentially of inner mass 22, as seen in FIG. 6, surrounded by an outer semipermeable wall 25. Wall 25 has a passageway 26 in it at the site of indentation 23b, seen in dashed lines. Passageway 26 extends through the semipermeable wall, and it was formed in the same manner as passageway 18 of device 17 described supra.

DETAILED DESCRIPTION OF THE INVENTION

In a presently preferred embodiment, the dispensing device of the invention is manufactured in the form of a pharmaceutical tablet. In this embodiment, the design shape and dimensions correspond to and present the appearance of tablets such as discoid, oval, oblong, round or square. The upper and lower surfaces of the device may be the same, or they may be different in shape and design. The surface may be flat, round, concave or convex. The tablet-shaped osmotic devices may be conventional sizes such as 3/16, 7/32, 11/32, 7/16 inches, and the like. The tablet can also have an elongated shape that corresponds to the size and shape of conventional oral capsules such as triple zero, double zero, zero, and one through eight. The final device can have its surface embossed with a symbol or letter which serves as a means for identifying the contents in the device, and the manufacturing source of the device.

The dispensing device is manufactured for delivering a drug formulation to a biological environment. The term drug as used herein broadly includes physiologically or pharmacologically active drugs that produce a local or systemic result. The term generically includes gastrointestinal, cardiovascular, respiratory, sympathomimetic, cholinomimetic, adregneergic, antimuscarine, skeletal muscle relaxants, diuretics, uterine, hormonal, vitamins, nutrients, anesthetic, sedative, hypontic, antiepiletic, psychopharmacologic, analgesic, antipyretic, antihistamine, central nervous system, antineoplastic, parasiticidic, and diagnostic drugs. The biological environment includes animals, which term animal embraces warm blooded animals, primates, humans, household, sport and farm animals. The amount of drug housed in the osmotic device is a dosage unit amount needed for a therapeutic regimen, with the device usually housing from 10 ng to 5 g of drug. The drugs preferably are present in their present conventional dose are disclosed in *Pharmaceutical Sciences*, by Remington, Fourteenth Edition, 1970, published by Mack Publishing Company, Easton, Pennsylvania, and in *The Pharmacological Basis of Therapeutics*, by Goodman and Gilman, Fourth Edition, 1970, published by the Macmillan Company, London, England.

In the osmotic dispensing device, the drug formulation is preferably present in the device in a form that exhibits an osmotic pressure gradient across a semipermeable wall against an external fluid. The osmotic pressure gradient generally is dependent on the solubility of the drug in the fluid that enters the device and the concentration difference across the semipermeable wall. The osmotic pressure gradient between the drug and the external fluid will cause fluid to be imbibed through the semipermeable wall into the device, creating a hydrostatic pressure inside the device that dispenses drug solution through the passageway to the environment. In those instances where the drug exhibits limited solubility in the external fluid imbibed into the device, an osmotically effective solute is added or mixed with the drug formulation. The osmotically effective solute or compound exhibit an osmotic pressure gradient across the semipermeable wall, and they function in the manner described supra. Typical osmotically effective solutes include magnesium sulfate, sodium chloride, calcium sulfate, and the like.

Wall forming materials used to form the wall of the osmotic device are semipermeable materials permeable to the passage of aqueous type fluids, including water and biological fluids, and they are substantially impermeable to the passage of drug and other ingredients housed in the device. Typical wall forming materials include semipermeable polymers such as cellulose acetate, cellulose diacetate, cellulose triacetate, cellulose acetate phthalate, polyurethane, and the like. The thickness of the wall, or the polymeric coating surrounding the solid drug mass is usually about 2.5 mils to 50 mils.

The indentation formed in the solid mass preferrably has a transverse dimension, a width, that is typically greater than twice the thickness of the coating applied to the solid mass. More usually, it will be about 5 times the thickness of the coating applied to he mass. For indentations whose transverse dimension vary, such as a conical indentation, the transverse dimension at the mouth of the indentation may be used in determining the above relationship to the coating thickness. The ratio of depth to width, of the indentation will typically be at least about 5:1 to 1:1 and more usually at least 2:1. In those embodiments where the transverse dimension vary, the transverse dimension at the mouth of the indentation may be used to determine the ratio. The general shape of the indentation may enjoy a wide variety of shapes. The indentation usually has a top even with the surface of the uncoated mass and a bottom pressed into the mass. For convience it normally will have a regular shape, such as cylindrical, conical, frustoconical, hemispherical, cubical, and the like. The indentation or recess may be formed by techniques such as impressing, drilling, laser penetration, and the like. The size of the outlet passageway, or hole in the wall of the device made in accordance with the invention generally will conform to the maximum and minimum sizes for passageways as disclosed by Theeuwes et al in U.S. Pat. No. 3,916,899. The dimensions of a passageway will usually exhibit a width of from about a micropore up to about 100 mils, at its visible entrance seen at the exposed surface of the wall.

The oral osmotic device or tablet may be manufactured by using such methods as wet granulation, dry granulation followed by compression and slugging techniques. The device can be coated with a semipermeable wall varying thickness by spray-gun coating, air suspension coating, fluidized bed coating, and the like. The oral device may be polished, colored and the like to esthetically enhance the appearance of the device. These procedures and similar manufacturing techniques are known to the art in *Remington's Pharmaceutical Sciences,* Fourteenth Edition, pages 1649 to 1968, 1970; in *The Theory and Practice of Industrial Pharmacy,* by Lachman, et al., pages 197 to 225, 1970, published by Lea and Febiger, Philadelphia, Pennsylvania, in *Manesty* Rotary Tablet Machine, Sections 1 through 5, 1972, published in Liverpool, England; and the air suspension techniques as disclosed in U.S. Pat. No. 2,799,241; in *J. Am. Pharm. Assoc.,* Vol. 48, pages 451 to 459, 1959; and ibid., Vol, 49, pages 82 to 84, 1960.

The following examples are merely illustrative of the present invention and the should not be considered as limiting the scope of the invention in any way, as these and other equivalents thereof will be more apparent to those versed in the art in the light of the present disclosure, the drawings and the accompanying claims.

EXAMPLE 1

An oral, osmotic dispensing device for the controlled dispensing of the drug formulation potassium chloride in the gastrointestinal tract of warm blooded animals is manufactured as follows: first, 500 mg. of USP grade potassium chloride is mixed with a trace of poly(vinyl pyrrolidone) and charged into a round mold having a concaved lower surface. The material is compressed with a 0.375 inch plunger having a convexed surface under an applied force of 2 tons. Then, after the plunger is removed from the mold, a second plunger equipped with a funnel-shaped cone is pressed into the compressed drug with a total force of $6 \times 10^3$ psi, with the drug mixture assuming the shape of the plunger at the drug-plunger interface. Next, the compressed drug with the prepassageway forming indenture is removed from the mold and placed in an air stream containing cellulose acetate having an acetyl content of 32% in acetone:water, in the ratio of 90:10, weight-to-weight, and the formulation is then surrounded with a 5 mil thick semipermeable wall. Simultaneously, the indentation is partly coated with a minimal deposit of cellulose acetate along its inner surface, and partially towards its bottom. The final formed hole extends through the wall and communicates with the drug for dispensing the drug to the exterior over time. The device is indicated for the management of hypokalemia and for use with diuretics such as the thiazides.

EXAMPLE 2

A series of osmotic therapeutic systems for the controlled and continuous release of drug over time are manufactured as follows: first, round molds having a diameter of 5/16 inches each are filled with drug formulation consisting of a blend of 125 mg of theophylline monoethanolamine, a trace of the cohesive binder sodium alginate, and a trace of magnesium stearate lubricant, and the formulation compressed with a plunger having a surface with a v-shaped indenture dye integrally formed as part of the plunger. The formulation is subjected to an applied force of $4 \times 10^3$ psi to yield a v-shaped indentation configuration in each compressed formulation. Next, the formulations are surrounded with a 6.5 mil thick semipermeable polymeric wall to form a compartment containing the drug. During the application of the wall, the semipermeable polymer partly coats the surface of the indentation thereby forming a passageway that extends through the wall and connects the drug with the exterior of the device. The wall is applied in a fluidized bed from cellulose acetate, 6% in methylene chloride:methanol solution, 80:20 weight:weight percent. The cellulose acetate has an acetyl content of 32%.

These series of osmotic devices are manufactured according to the instant example; these devices have final passageways of 15 mils, 25 mils, and 42 mils in diameter through the 6.5 mil wall. Accompanying FIGS. 8 and 9 are set forth to illustrate, as seen in FIG. 9, the results obtained for this invention compared with a mechanically drilled passageway as seen in FIG. 8.

Figure 8:
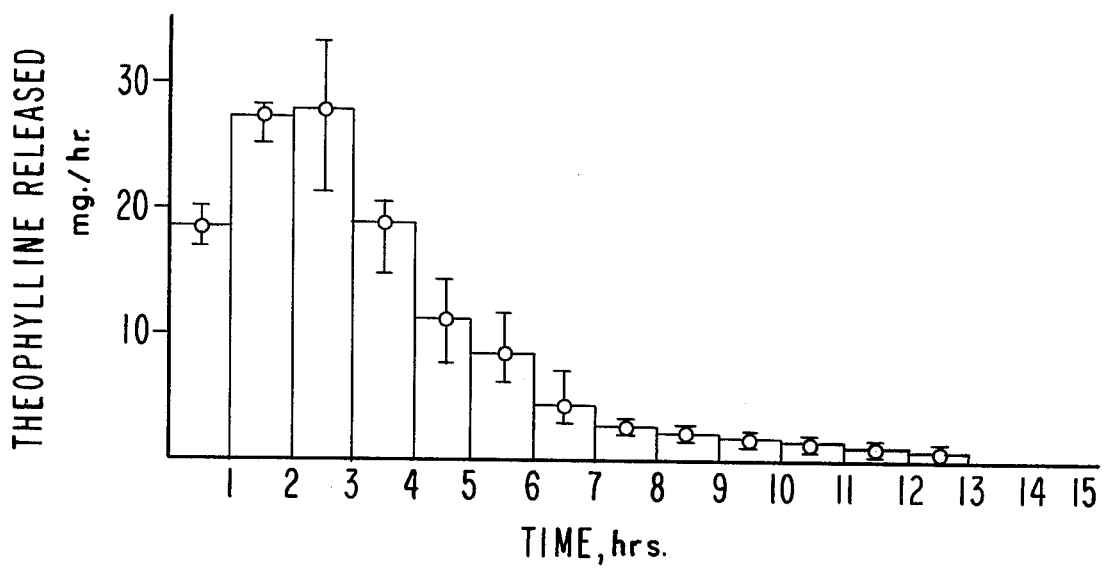
FIG. 8 is a graph illustrating the rate of release of drug versus time from a prior art osmotic device having a passageway formed by mechanically drilling it through the wall; and, FIG. 9 is a graph of the release rate of drug versus time from an osmotic device made according to the invention.
Figure 9:
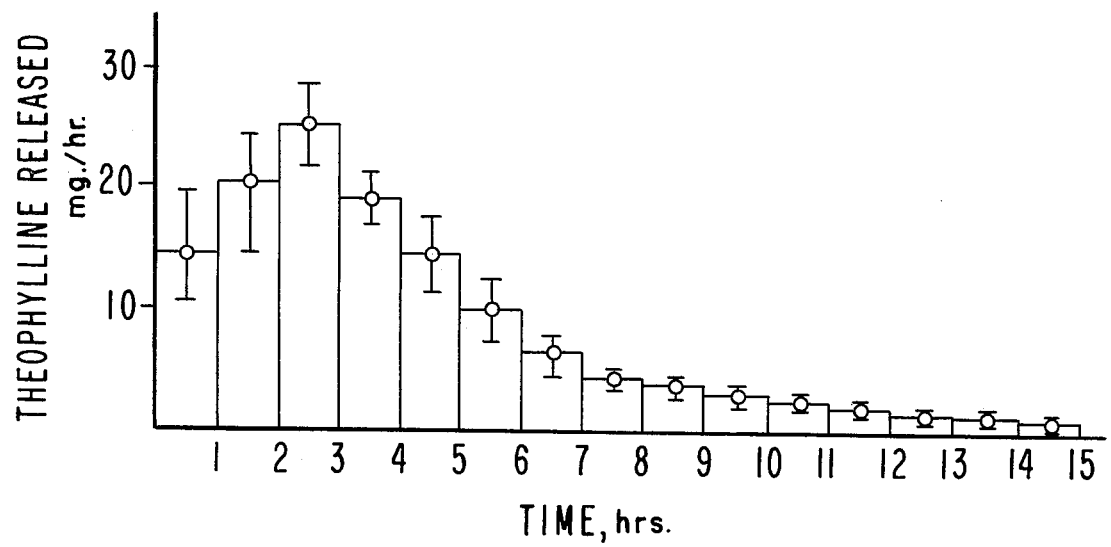

FIGS. 8 and 9 depict the rate of release in mg/hr for theophylline expressed as the free base. In FIG. 8 the release rate is from an osmotic device having a drilled passageway 25 mil in diameter. In FIG. 9 the release rate is from an osmotic device having a passageway 25 mil in diameter formed during the wall coating manufacturing step of the device. The drug theophylline dispensed from the device is indicated for the treatment as a diuretic, in the treatment of angina pectoris, status asthmaticus and paroxysmal nocturnal dyspnea.

EXAMPLE 3

Osmotically driven devices for the controlled administration of theophylline orally were made as follows: first, spherical molds having a diameter of approximately 1 cm were filled with a homogeneous blend of 125 mg of theophylline monoethanolamine, a trace of sodium alginate and a trace of magnesium stearate. Then, the blends were compressed into spherical solid drug formulaton masses. Next, the masses were removed from the molds and cylindrical holes 25 mils in diameter and 50 mils deep, 37 mills in diameter and 70 mils deep and 52 mils in diameter and 100 mils deep were drilled into the solid masses. The masses were coated in a fluidized bed with cellulose acetate, 6% in methylene chloride:methanol solution, 80:20 weight:-weight percent. The resulting coatings were about 6.8 mils thick on each mass. The diameter of the final hole or passageway through the coated polymer was respecfully 14.8 mils, 25.3 mils and 41.7 mils. The final diameter represents a decrease of about 20 to 40% from the initial diameter of the uncoated mass.

The novel process of this invention uses means for manufacturing a passageway in a dispensing device that leads to the obtainment of a precise release rate in the environment of use, while simultaneously maintaining the integrity and character of the system. While there have been described and pointed out features of the invention as applied to presently preferred embodiments, those skilled in the art will appreciate that various modifications, changes, additions and omissions in the manufacture illustrated and described can be made without departing from the spirit of the invention.

I claim:

1. A process for forming an osmotic delivery device comprising:
   (a) compressing a drug formulation into a solid mass;
   (b) forming an indentation having predetermined dimensions in the solid mass; and
   (c) thereafter coating the solid mass with a wall forming material which in final form is an osmotic membrane which covers the solid mass and is permeable to aqueous and biological fluids and substantially impermeable to the drug formulation, whereby the predetermined dimensions of the indentation are selected such that a passageway is formed from the solid mass through the formed wall to the exterior of the osmotic delivery service.

2. The process of claim 1 wherein the indentation has a top even with the surface of the uncoated solid mass and a bottom pressed into the solid mass and which indentation is partly coated with the wall forming material during the coating of the mass with its bottom remaining substantially free of wall forming material.

3. The process of claim 1 wherein the wall forming material is a polymeric composition.

4. The process of claim 1 wherein the coating is carried out in a fluidized bed.

5. The process of claim 1 wherein the coating process used to surround the solid mass with the wall forming material is an air suspension process.

6. The process of claim 1 wherein the drug formulation is compressed into a solid mass which is sized, shaped and adapted for oral administration to a human.

7. The process of claim 1 wherein the drug formulation compressed into the solid mass exhibits an osmotic pressure gradient across the wall against an external fluid.

8. The process of claim 1 wherein the passageway extends through the wall and exhibits a width of from about a micropore up to about 100 mils.

9. A two-step process for forming an osmotic delivery device comprising:
   (a) simultaneously compressing a drug formulation into a solid mass and forming an indentation in said mass, said indentation having predetermined dimensions; and
   (b) thereafter coating the solid mass with a wall forming material which in final form is an osmotic membrane which covers the solid mass and is permeable to aqueous and biological fluids and substantially impermeable to the drug formulation, whereby the predetermined dimensions of the indentation are selected such that a passageway is formed from the solid mass through the formed wall to the exterior of the osmotic delivery device.

10. The process according to claim 9 wherein the wall forming material is a semipermeable polymer.

11. The process of claim 9 wherein the drug formulation exhibits an osmotic pressure gradient against an external fluid.

12. The process of claim 9 wherein the passageway exhibits a width of from about a mocropore up to about 100 mils.

13. The process of claim 9 wherein the coating process is a fluidized bed coating process.

14. The process of claim 9 wherein the coating process is an air suspension process.

15. The process of claim 9 wherein the solid mass is sized, shaped and adapted for oral administration to a human.

* * * * *